United States Patent [19]

Pandit et al.

[11] Patent Number: 4,933,360
[45] Date of Patent: Jun. 12, 1990

[54] NOVEL CHLORTHALIDONE PROCESS AND PRODUCT

[75] Inventors: Nivedita Pandit, Middlebury; Stephen T. Horhota, Brookfield, both of Conn.

[73] Assignee: Boehringer Ingelheim Pharmaceuticals, Inc., Ridgefield, Conn.

[21] Appl. No.: 796,467

[22] Filed: Nov. 8, 1985

Related U.S. Application Data

[63] Continuation of Ser. No. 581,869, Feb. 27, 1984, abandoned, and a continuation-in-part of Ser. No. 475,898, Mar. 16, 1983, abandoned.

[51] Int. Cl.$^5$ ............................................. A01N 43/38
[52] U.S. Cl. ....................................... 514/417; 424/4; 424/80
[58] Field of Search ........................................ 514/417

[56] References Cited

U.S. PATENT DOCUMENTS

4,128,632 12/1978 Lo et al. ................................ 514/622
4,151,273 4/1979 Riegelman et al. ................... 424/78
4,344,934 8/1982 Martin et al. ......................... 424/80

FOREIGN PATENT DOCUMENTS

0125420 4/1984 European Pat. Off. ............. 514/417

OTHER PUBLICATIONS

S. Ibrahim and S. Shawky, Exp.-Congr. Technol. Pharm., 3rd, 5, pp. 203–210, 1983.
S. Ibrahim and S. Shawky, Exp.-Congr. Technol. Pharm., 3rd, 5, pp. 193–202, 1983.
Eide et al., *Acta Pharm. Suecica*, 4, 201–210, (1967).
Eide et al., *Acta Pharm. Suecica*, 4, 185–200, (1967).
Anderson et al., *J. Pharm. Sci.*, 58, 1425–1427, (1969).
Simonelli et al., *J. Pharm. Chem.*, 65, 355–361, (1976).
Sugimoto et al., *Drug Development and Industrial Pharmacy*, 6, 137–160, (1980).
Higuchi, et al., *J. Am. Pharm. Assoc.*, 43, 393–397, (1954).
Plazier-Vercammen et al., *J. Pharm. Sci.*, 69, 1403–1408, (1980).
Horn et al., *J. Pharm Sci.*, 71, 1021–1226, (1982).
Plazier-Vercammin, *J. Pharm. Sci.*, 72, 1042–1044, (1983).
Paudit et al., *J. Pharm. Sci.*, 74, 857–861, (1985).
MacGregor et al., *J. Pharm. Sci.*, 74, 851–856, (1985).
Farina et al., *J. Pharm. Sci.*, 74, 995–998, (1985).
Vardan et al., *JAMA*, 258, 484–488, (1987).
Translation-Pharm. Acta. Helv. 58, 14–22, (1983), Bloch et al.
Chem. Abstracts, vol. 103, entry 92730j.
Chem. Abstracts, vol. 95, entry 138519u, Bogdanova et al.
Journal of Pharm. Sci., Sep. 71, vol. 60, No. 9, pp. 1281–1302, Chiou et al.
Chem. Abstracts, vol. 98, entry 113628c, Bloch et al., 1983.

*Primary Examiner*—Joseph L. Schafer
*Assistant Examiner*—Peter F. Kulkosky
*Attorney, Agent, or Firm*—David E. Frankhouser; Daniel Reitenbach; Mary-Ellen M. Timbers

[57] ABSTRACT

Water-soluble dispersions of chlorthalidone are prepared by a process comprising:
(a) forming a solution comprising a water soluble pharmaceutically acceptable polymeric carrier and a $C_1$–$C_4$ alkanol,
(b) dissolving chlorthalidone in the solution thus formed, and
(c) removing the $C_1$–$C_4$ alkanol from the solution by evaporation, the amount of said carrier being effective to suppress substantially the formation of the alkyl ether by-product from the reaction of chlorthalidone with the $C_1$–$C_4$ alkanol. A preferred water soluble carrier is polyvinylpyrrolidone and a preferred $C_1$–$C_4$ alkanol is methanol.

11 Claims, No Drawings

NOVEL CHLORTHALIDONE PROCESS AND PRODUCT

This is a continuation, of application Ser. No. 06/581,869, filed Feb. 27, 1984 now abandoned and a continuation-in-part of patent application Ser. No. 475,898, filed March 16, 1983 now abandoned.

Chlorthalidone is a well-known diuretic agent which has been widely marketed since the early 1960's. Chlorthalidone, however, has limited aqueous solubility (~120 $\mu$g/ml) and accordingly is not well absorbed from the human gastrointestinal tract. The high melting point of chlorthalidone (225° C.) suggests that chlorthalidone crystals have a very high lattice energy which may hinder dissolution and thereby decrease absorption from gastrointestinal fluids. A need exists, therefore, for finding methods for increasing the dissolution of chlorthalidone and thereby increasing bioavailability.

It is known that significant improvement in the dissolution and bioavailability of various pharmaceutical active ingredients having poor solubility can be achieved using solid state dispersion techniques as described in general by W. L. Chiou et al., *J. Pharm. Sci.*, 60, 1281 (1971) and S. Riegelman et al., U.S. Pat. No. 4,151,273. As defined in the Chiou article the term "solid state dispersion" means "a dispersion of one or more active ingredients in an inert carrier or matrix at solid state prepared by the melting (fusion), solvent, or melting-solvent method." The dispersion of an active ingredient in a solid carrier or diluent by traditional mechanical mixing is not included within the definition of the term. Solid state dispersions may also be called "solid dispersions," "solid solutions, " or "coprecipitates," the last term being used frequently to refer to solid state dispersions obtained by the solvent method.

Solid state dispersions of chlorthalidone in urea, prepared by the fusion method, have been reported by D. Bloch et al., *Pharm. Acta. Helv.*, 57, 231 (1982) as showing enhanced dissolution characteristics.

In the "solvent method" for preparing solid state dispersions, the active ingredient is conventionally dispersed in a water soluble carrier by dissolving a physical mixture containing the active ingredient and the carrier in a common organic solvent and then removing the solvent by evaporation. The resulting solid dispersion is recovered and used in the preparation of suitable pharmaceutical formulations using conventional methods.

Various water soluble carriers are known in the art to be useful for preparing solid state dispersions containing pharmaceutical agents using the solvent method. Examples of such carriers include water soluble pharmaceutically acceptable polymers such as polyvinylpyrrolidone (PVP) and polyethylene glycol (PEG).

Many organic solvents are useful in the solvent method for preparing solid state dispersions preferably the solvent should be: (a) capable of dissolving both the active ingredient and the carrier, (b) chemically inert with respect to the active ingredient and the carrier, and (c) be sufficiently volatile to permit facile removal by evaporation using conventional techniques.

Alkanols having from one to four carbon atoms would in general be expected to be useful for preparing solid state dispersions by the solvent method. However it is known in the art that the lower alkanols, in particular methanol and ethanol, are capable of reacting with chlorthalidone to form alkyl ethers according to the reaction depicted below where R is $C_1$–$C_4$ alkyl:

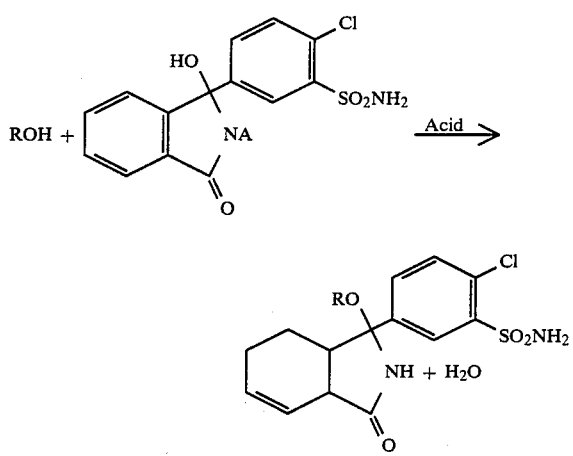

The above reaction is described in the literature by W. Graf et al., *Helv. Chim. Acta.*, 42, 1085 (1959) and M. Auterhoff et al., *Arch. Pharm.*, 312, 876 (1979). In view of the reactivity of the lower alkanols to chlorthalidone, one skilled in the art would not have been motivated to employ the lower alkanols, in particular methanol and ethanol, as a solvent in the solvent method for preparing water soluble solid state dispersions of chlorthalidone especially since commercial samples of chlorthalidone may contain acetic acid as an impurity.

The present invention provides a method for preparing pharmaceutically acceptable water soluble solid state dispersions of chlorthalidone by the solvent method using a $C_1$–$C_4$ alkanol, in particular methanol or ethanol, without the substantial formation of alkyl ethers as degradation products. In particular, the present invention comprehends a process for preparing a water soluble pharmaceutically acceptable solid state dispersion of chlorthalidone which comprises:

(a) forming a solution comprising a water soluble pharmaceutically acceptable polymeric carrier and a $C_1$–$C_4$ alkanol, (b) dissolving chlorthalidone in the solution thus formed, and (c) removing the $C_1$–$C_4$ alkanol from the solution by evaporation, the amount of said carrier being effective to suppress substantially the formation of the alkyl ether by-product from the reaction of chlorthalidone with the $C_1$–$C_4$ alkanol.

Solid state dispersions of chlorthalidone prepared by using methanol as the common solvent and polyvinylpyrrolidone (PVP) as the water soluble pharmaceutically acceptable carrier (one part by weight of PVP to two parts by weight of chlorthalidone) when administered to humans as 25-mg tablets were shown to provide significantly higher blood levels, faster peak levels, and greater areas under the curve (AUCs) as compared to commercially available Hygroton ® Tablets.

The polymeric carrier used in the process of the invention must be pharmaceutically acceptable and be substantially soluble both in water and in the particular $C_1$–$C_4$ alkanol selected for use in the process. Moreover, the polymeric carrier must be capable of forming a solid state dispersion of chlorthalidone after removal of the alkanol, and be capable of suppressing ether formation arising from reaction of the chlorthalidone with the $C_1$–$C_4$ alkanol, as discussed above. The ability of a polymeric carrier to suppress ether formation can be determined routinely by dissolving chlorthalidone in a $C_1$–$C_4$ alkanol, such as methanol, in a glass container in the presence and absence of the polymeric carrier and analyzing aliquots of the solution (taken at varying times up to 24 hours) for chlorthalidone content by HPLC techniques. An acceptable loss of chlorthalidone is up to about 2% after 24 hours at 40° C.

A preferred polymeric carrier is polyvinylpyrrolidone (PVP), the general use of which to prepare solid state dispersions of pharmaceutical active ingredients is described by the Chiou reference, supra. As previously discussed herein, the literature suggests that the reaction of chlorthalidone and methanol to form ether by-products is catalyzed by strong acids such as hydrochloric or sulfuric acid. Evidence has now been obtained which demonstrates that the reaction between chlorthalidone and methanol is also catalyzed by trace amounts of heavy metal ions such as iron or nickel ions, which may be present as trace impurities in commercially available chlorthalidone or may be present from the use of processing equipment fabricated from iron or ferro alloys such as stainless steel. Although it has now been found that acetic acid, which may be present in commercially available samples of chlorthalidone, does not itself catalyze the reaction forming ether by-products, evidence suggests that acetic acid can enhance the catalytic effect of heavy metal ions on ether formation. It is believed that PVP suppresses the formation of ethers primarily by complexing trace amounts of heavy metal ions thus making them unavailable for catalysis. The suppression of ether formation may to a lesser extent also be attributed to a protective effect arising from formation of a chemical complex between chlorthalidone and PVP or to a medium effect at high PVP concentrations.

The amount of polymeric carrier employed in the process of the invention must be sufficient to suppress substantially the formation of ether by-products when chlorthalidone is mixed with the $C_1$–$C_4$ alkanol and to provide a water soluble solid state dispersion of chlorthalidone after removal of the alkanol.

Using methanol the amount of PVP employed in the process of the invention must be at least 20% by weight (one part of PVP to four parts of chlorthalidone) of the total combined weight of the chlorthalidone and PVP. A range of about 20% to about 99% (one part PVP to 100 parts of chlorthalidone) by weight of PVP of the total combined weight of PVP and chlorthalidone can be employed. A range of from about 20% to about 66% (one part of PVP to 0.5 parts of chlorthalidone) by weight of PVP is preferred. Using glass-lined equipment the optimum weight of PVP is about 25% by weight (one part of PVP to three parts of chlorthalidone). Using stainless steel equipment, it is necessary to use more PVP for optimum results, and about 33% by weight of PVP (one part of PVP to two parts of chlorthalidone) is most preferred.

The amount of the $C_1$–$C_4$ alkanol employed in the process of the invention should be sufficient to solubilize both the polymeric carrier and chlorthalidone. It will be apparent to those skilled in the art that best results will be achieved on a large scale using as high a concentration of chlorthalidone as is possible. Thus, optimally the process should be carried out using concentrations of chlorthalidone at the upper limits of solubility. The apparent equilibrium solubility of chlorthalidone at 26° C. in various alkanols is as follows: methanol—76.1 mg/ml: ethanol—15.5 mg/ml; isopropanol—3.2 mg/ml.

In order to completely solubilize the chlorthalidone in the solution of the polymeric carrier in the appropriate $C_1$–$C_4$ alkanol, it may be necessary to heat the initial mixture. For example, using methanol the mixture formed by adding chlorthalidone to the solution of the polymeric carrier in the $C_1$–$C_4$ alkanol (in particular PVP in methanol) can be heated at a temperature ranging from about 55°–58° C. to effect complete solution. It should be appreciated by those skilled in the art that PVP itself can increase the solubility of chlorthalidone in the $C_1$–$C_4$ alkanol.

The order of addition of chlorthalidone and the polymeric carrier is critical to suppress ether formation. It is essential that the polymeric carrier is dissolved in the $C_1$–$C_4$ alkanol to form a solution before chlorthalidone comes in contact with the alkanol. If a physical mixture of chlorthalidone and the polymeric carrier is added to the $C_1$–$C_4$ alkanol (as described by Chiou, supra), ether formation is not adequately suppressed. Likewise, if chlorthalidone is first dissolved in the $C_1$–$C_4$ alkanol to form a solution, and the polymeric carrier is then added, ether formation is not adequately suppressed. When the chlorthalidone is added to a solution of the polymeric carrier in the $C_1$–$C_4$ alkanol ether formation is substantially suppressed, and the solid state dispersion after evaporation of the $C_1$–$C_4$ alkanol will not contain substantial amounts of undesirable ether by-products.

Once the chlorthalidone is added to the solution comprising the polymeric carrier and the $C_1$–$C_4$ alkanol, the solution will be stable to ether formation for at least one hour with continued heating and for at least four days at room temperature. During normal processing using methanol and PVP, the temperature will only need to be held at 55° C. for about ten minutes to allow complete solution of chlorthalidone.

The $C_1$–$C_4$ alkanols used in the process of the present invention are saturated organic mono-alcohols having from one to four carbon atoms, i.e., methanol ethanol, n-propanol, isopropanol, n-butanol, isobutanol, or tert-butanol. Methanol and ethanol are preferred. Methanol is most preferred because it is capable of dissolving chlorthalidone at higher concentrations.

It will be understood by those skilled in the art that the process of the present invention can be carried out in the presence of a chelating agent, for example, ethylenediamine tetraacetic acid (EDTA), which can complex and further reduce the amount of trace heavy metals present in solution. When EDTA is used with methanol as the solvent, water (at least 5%) must also be included in the solution to solubilize the EDTA. This, however, lowers the solubility of chlorthalidone thereby increasing the amount of methanol required. By using a chelating agent in combination with the polymeric carrier, the amount of the polymeric carrier can be reduced. The selection and use of a particular chelating agent will be apparent to those skilled in the art.

Recovery of the solid state dispersion of chlorthalidone from the solution formed by dissolving chlorthalidone in a solution of the polymeric carrier in the $C_1$–$C_4$ alkanol can be carried out using procedures conventional in the art for evaporating solvents. The dried water soluble solid state dispersion of chlorthalidone can be used directly as a diuretic or, if desired, it can be incorporated into conventional pharmaceutical solid dosage forms, such as tablets or capsules, using conventional pharmaceutical procedures or techniques. In a preferred method for recovering the solid state dispersion of chlorthalidone in PVP from methanol, the methanol solution containing chlorthalidone and PVP is spray coated onto lactose (or other suitable excipient) using a fluid bed granulator by conventional techniques to give a free flowing powder in which the lactose particles are surrounded by a coating of the solid state dispersion. The resulting solid state dispersion can be incorporated into conventional solid pharmaceutical formulations (e.g. tablets or capsules) using methods known in the pharmaceutical art.

When a fluid bed granulator is used to remove methanol from solutions containing chlorthalidone and PVP, the product temperature employed during processing may influence both the ether content and the methanol content of the final product. Best results are obtained using a combination of spray rate and inlet air temperature to maintain the product temperature between 45° and 55° C.

If desired residual methanol can be removed by spraying water onto the lactose-coated product in the fluid bed granulator. Best results are obtained using a combination of spray rate and inlet air temperature to maintain a product temperature between 28° and 32° C.

Pharmaceutical compositions suitable for employing the solid state dispersions of chlorthalidone prepared as hereindescribed will be apparent to those skilled in the art. The compositions can be preferably tablets or capsules and can contain other conventional inert carriers or excipients such as lubricants, disintegrating agents, fillers, coatings, etc. For tablets containing a solid state dispersion of chlorthalidone in PVP, coated onto lactose particles, preferred excipients are: microcrystalline cellulose, sodium starch glycolate, colloidal silicon dioxide, and magnesium stearate. Preferably, the amount of chlorthalidone in a tablet can range from about 5 mg to about 25 mg. A compressed tablet containing 25 mg of chlorthalidone is presently being marketed. The usual daily dosage of chlorthalidone is 0.2 to 1.3 mg/kg.

The present invention also contemplates a method for inducing diuresis in a warm-blooded animal, including humans, which comprises administering to said animal a solid state dispersion of chlorthalidone prepared by the process of this invention as herein-described in an amount sufficient to induce diuresis. In a preferred method, the solid state dispersion employs PVP as the dispersing agent, and the dispersion is spray coated onto lactose particles. It is preferred to use the solid state dispersion, or the solid state dispersion spray coated onto lactose, in a compressed tablet containing other pharmaceutically acceptable excipients.

The following examples illustrate specific embodiments of the present invention. However, it is to be understood that the invention is not intended to be limited to the specific embodiments hereinafter described:

EXAMPLE 1

A. A solution of 666.0 g of polyvinylpyrrolidone (PVP) in 25 l of methanol is prepared by adding PVP to methanol in a glass vessel. To the solution is added 2000.0 g of chlorthalidone. The mixture is heated to 55°-58° C. to dissolve the chlorthalidone. Upon cooling to room temperature, the resulting solution is spray coated onto 5334.0 g of lactose using a fluid bed granulator (Glatt WSG-5). The temperature conditions and the spray rate used for the spray coating process are as follows:

Inlet air temPerature: 100° C.
Solution spray rate: 137 ml/min
Average product temperature during processing: 70° C.
Final product temperature: 80° C.

B. A solution of 2000.0 g of chlorthalidone in 25 l of methanol is prepared by adding chlorthalidone to methanol and heating the mixture to 55°-58° C. To the solution is added 666.0 g of PVP. The resulting solution is spray coated onto lactose using a fluid bed granulator under process conditions similar to those described in Part A.

C. The dry solid state dispersion products obtained in Part A and Part B were analyzed for chlorthalidone and chlorthalidone methyl ether content. The product obtained as described in Part A showed that about 0.8% of the chlorthalidone was converted to the methyl ether, while the product obtained as described in Part B showed that about 37% was converted to the methyl ether. The dry products obtained as described in Part A and Part B were filled into hard gelatin capsules in an amount equivalent to 25 mg of chlorthalidone. When administered to beagle dogs the product from Part A gave a significantly higher blood level, faster time to peak, and greater areas under the curve (AUCs) as compared to commercially available Hygroton ® Tablets (25 mg). When similarly administered to dogs, the product from Part B gave significantly lower blood levels and less fast time to peak as compared to the product from Part A.

EXAMPLE 2

A solution of 2.5 kg of polyvinylpyrrolidone (PVP) in 363 l of methanol is prepared by adding PVP to methanol in a stainless steel vessel. To the solution is added 45 kg of chlorthalidone. The mixture is heated to 55° C. to dissolve the chlorthalidone. After holding the solution at 55° C. for one hour, the solution is cooled and held at room temperature for 18 hours. The solution is then spray coated onto 112.5 kg of lactose (USP Fast Flo) using a fluid bed granulator (Glatt WSG-120). The temperature conditions and the spray rate used for the spray coating process are as follows:

Inlet air temperature: 60° C.
Solution spray rate: 1.0 l/min
Average product temperature during processing: 49° C.
Final product temperature*: 75° C.

*Heating was continued at an inlet air temperature of 84° C. for ten minutes after completion of the spraying process.

The product obtained from the spray coating process had the following analysis:

| | |
|---|---|
| Chlorthalidone | 240 mg/g |
| Chlorthalidone methyl ether | 0.9 mg/g |
| Chlorthalidone carboxylic acid | .0 mg/g |
| Residual Methanol | 1.8% (W/W) |
| Dissolution (% dissolved in 10 minutes) | 100% |

EXAMPLE 3

The following procedure illustrates water treatment of the product on the fluid bed granulator to remove residual methanol.

A 139.3-kg batch of chlorthalidone/PVP dispersion on lactose (prepared from three separate lots of material) is sprayed with water in the fluid bed granulator using the following temperatures and process conditions:

Inlet air temperature: 85° C.
Spray rate: 1800 ml/min
Average product temperature during processing: 31° C.
Final product temperature: 65° C.
Total quantity of water sprayed: 300 kg
Total elapsed spraying time: 3.25 hr
Analysis of the product before and after water treatment gave the following results:

|  | Initial | Final |
| --- | --- | --- |
| Methanol (ppm) | 7400 | 172 |
| Chlorthalidone (mg/g) | 231 | 248 |
| Chlorthalidone methyl ether (mg/g) | 0.6 | 0.6 |
| Chlorthalidone hydrolysis product (mg/g) | 0.3 | 0.4 |

EXAMPLE 4

Tablets containing 25 mg of chlorthalidone are prepared by conventional direct compression methods. A preferred formulation for the tablets is set forth below:

|  | Amount (mg/tablet) |
| --- | --- |
| Chlorthalidone/PVP dispersion spray coated on lactose. 250 mg/chlorthalidone (prepared using a ratio by weight of 1 part PVP to 2 parts chlorthalidone) | 100.00 |
| Micro-crystalline cellulose NF | 44.5 |
| Sodium starch glycolate NF | 6.0 |
| Colloidal silicon dioxide NF | 2.0 |
| Magnesium Stearate USP | 0.5 |
| Theoretical Tablet Weight | 153.0 mg |

What is claimed is:

1. A process for preparing a water soluble pharmaceutically acceptable solid state dispersion of chlorthalidone which comprises:
   (a) forming a solution of polyvinylpyrrolidone in a $C_1$–$C_4$ alkanol,
   (b) dissolving chlorthalidone in the solution thus formed, and
   (c) removing the $C_1$–$C_4$ formed from the solution by evaporation, the ratio by weight of polyvinylpyrrolidone to chlorthalidone in the dispersion being in the range of from 1:4 to 1:05.

2. A process as defined in claim 1 wherein the $C_1$–$C_4$ alkanol is methanol.

3. A process as defined in claim 1 wherein the ratio by weight of polyvinylpyrrolidone to chlorthalidone is from 1:3 to 1:2.

4. A process as defined in claim 2 wherein the methanol is evaporated from the solution by spray coating the solution onto lactose particles.

5. A solid state dispersion of chlorthalidone produced by the process of claim 1.

6. A pharmaceutically acceptable diuretic tablet composition comprising:
   (a) a diuretic effective amount of a solid state dispersion of chlorthalidone spray coated onto lactose particles according to the process of claim 4, and
   (b) a pharmaceutically acceptable tableting excipient.

7. A method of inducing diuresis in the warm-blooded animal comprising administering to said animal a solid state dispersion of chlorthalidone as defined in claim 5, the amount of chlorthalidone in said dispersion being effective for inducing diuresis.

8. A process as defined in claim 3 wherein the $C_1$–$C_4$ alkanol is methanol.

9. A process as defined in claim 8 wherein the methanol is evaporated from the solution by spray coating the solution onto lactose particles.

10. A solid state dispersion of chlorthalidone as defined in claim 5 wherein the dispersion is produced by the process of claim 8.

11. A solid state dispersion of chlorthalidone as defined in claim 5 wherein the dispersion is produced by the process of claim 9.

* * * * *

UNITED STATES PATENT AND TRADEMARK OFFICE
CERTIFICATE OF CORRECTION

PATENT NO. : 4,933,360
DATED : June 12, 1990
INVENTOR(S) : Nivedita Pandit, et al.

It is certified that error appears in the above-indentified patent and that said Letters Patent is hereby corrected as shown below:

In Claim 1, Column 6, Line 18 of the Patent, change "1:05" to -- 1:0.5 --.

Signed and Sealed this

Fifteenth Day of July, 1997

*Attest:*

BRUCE LEHMAN

*Attesting Officer*   Commissioner of Patents and Trademarks